United States Patent
Brennan et al.

(10) Patent No.: US 10,838,236 B2
(45) Date of Patent: *Nov. 17, 2020

(54) HIGH PLUS TREATMENT ZONE LENS DESIGN AND METHOD FOR PREVENTING AND/OR SLOWING MYOPIA PROGRESSION

(71) Applicant: Johnson & Johnson Vision Care, Inc., Jacksonville, FL (US)

(72) Inventors: Noel A. Brennan, Jacksonville, FL (US); Khaled Chehab, Jacksonville, FL (US); Xu Cheng, St. Johns, FL (US); Michael J. Collins, Jollys Lookout (AU); Manwai Charis Lau, Jacksonville, FL (US); Eric R. Ritchey, St. Johns, FL (US); Xin Wei, Jacksonville, FL (US)

(73) Assignee: Johnson & Johnson Vision Care, Inc, Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/421,843

(22) Filed: May 24, 2019

(65) Prior Publication Data

US 2019/0278106 A1    Sep. 12, 2019

Related U.S. Application Data

(60) Continuation of application No. 15/461,869, filed on Mar. 17, 2017, now Pat. No. 10,359,646, which is a
(Continued)

(51) Int. Cl.
*A61F 2/16* (2006.01)
*G02C 7/04* (2006.01)
(Continued)

(52) U.S. Cl.
CPC .............. *G02C 7/066* (2013.01); *A61F 2/142* (2013.01); *A61F 2/145* (2013.01); *A61F 2/16* (2013.01);
(Continued)

(58) Field of Classification Search
CPC .................... A61F 2/145; A61F 2/1451; A61F 2/1613–2/1618; A61F 2250/0053;
(Continued)

(56) References Cited

U.S. PATENT DOCUMENTS

| 4,575,205 A | * | 3/1986 | Rappazzo | ............... G02C 7/04 351/159.02 |
| 4,932,971 A | | 6/1990 | Kelman | |

(Continued)

FOREIGN PATENT DOCUMENTS

| EP | 1967892 A1 | 9/2008 |
| EP | 2988161 | 2/2016 |

(Continued)

OTHER PUBLICATIONS

European Search report for corresponding EPA No. 17208227.3 dated Mar. 29, 2018.
Ardaya et al. Optometry vol. 75, No. 3, Mar. 2004 pp. 169-174.

*Primary Examiner* — Paul B Prebilic

(57) ABSTRACT

Contact lenses incorporate high plus or add power profiles that at least one of slow, retard or preventing myopia progression and minimize halo effect. The lens includes a center zone with a negative power for myopic vision correction; and at least one treatment zone surrounding the center zone, the at least one treatment zone having a power profile that increases from an outer margin of the center zone to a positive power within the at least one treatment zone of greater than +5.00 D.

5 Claims, 9 Drawing Sheets

Related U.S. Application Data division of application No. 14/464,182, filed on Aug. 20, 2014, now Pat. No. 9,638,936.

(51) Int. Cl.
*G02C 7/06* (2006.01)
*A61F 2/14* (2006.01)

(52) U.S. Cl.
CPC .............. *A61F 2/1618* (2013.01); *G02C 7/04* (2013.01); *G02C 7/041* (2013.01); *G02C 7/044* (2013.01); *G02C 7/048* (2013.01); *G02C 7/06* (2013.01); *G02C 2202/24* (2013.01)

(58) Field of Classification Search
CPC ... A61F 2250/0091; G07C 7/041; G07C 7/06; G07C 7/044; G07C 7/048; G07C 2202/24; G02C 7/041; G02C 7/06; G02C 7/044; G02C 7/048; G02C 2202/24
See application file for complete search history.

(56) References Cited

U.S. PATENT DOCUMENTS

| | | | |
|---|---|---|---|
| 5,384,606 A | 1/1995 | Koch | |
| 5,702,440 A | 12/1997 | Portney | |
| 6,045,578 A | 4/2000 | Collins et al. | |
| 7,025,460 B2 | 4/2006 | Smith et al. | |
| 8,480,229 B2 | 7/2013 | Gerligand | |
| 9,638,936 B2 * | 5/2017 | Brennan | A61F 2/142 |
| 10,061,143 B2 | 8/2018 | Brennan et al. | |
| 10,359,646 B2 * | 7/2019 | Brennan | |
| 2004/0169820 A1 | 9/2004 | Dai | |
| 2005/0041203 A1 | 2/2005 | Lindacher | |
| 2008/0218687 A1 | 9/2008 | Phillips | |
| 2009/0141235 A1 | 6/2009 | Collins et al. | |
| 2010/0036489 A1 | 2/2010 | Lindacher | |
| 2010/0073629 A1 | 3/2010 | Menezes | |
| 2010/0097569 A1 * | 4/2010 | Weeber | A61F 2/1618 351/159.44 |
| 2010/0328604 A1 | 12/2010 | Collins | |
| 2011/0313058 A1 * | 12/2011 | Neitz | G02C 7/061 514/789 |
| 2012/0062836 A1 | 3/2012 | Tse | |
| 2012/0113386 A1 | 5/2012 | Back | |
| 2012/0194780 A1 * | 8/2012 | Back | G02C 7/041 351/159.73 |
| 2013/0250235 A1 * | 9/2013 | Foulds | G02C 7/104 351/159.65 |
| 2013/0278888 A1 | 10/2013 | Bakaraju et al. | |
| 2014/0211147 A1 | 7/2014 | Wei | |
| 2016/0054587 A1 | 2/2016 | Brennan et al. | |
| 2016/0054588 A1 | 2/2016 | Brennan et al. | |
| 2017/0115509 A1 * | 4/2017 | Brennan | G02C 7/042 |
| 2019/0227342 A1 * | 7/2019 | Brennan | G02C 7/044 |
| 2020/0150455 A1 * | 5/2020 | Bakaraju | G02C 7/04 |

FOREIGN PATENT DOCUMENTS

| | | |
|---|---|---|
| EP | 2988161 A1 | 2/2016 |
| JP | 2009540373 | 11/2009 |
| JP | 2012531630 | 12/2012 |
| JP | 2013537317 | 9/2013 |
| WO | WO2010019397 A2 | 2/2010 |
| WO | WO2010100523 A1 | 9/2010 |
| WO | WO2012034265 A1 | 3/2012 |
| WO | WO2008144497 A1 | 10/2012 |
| WO | WO2012173891 | 12/2012 |
| WO | WO2013101793 A1 | 7/2013 |
| WO | WO2014089612 A1 | 6/2014 |

\* cited by examiner

Group average

PSF Xsection; EP-6mm

Image Xsection; EP-6mm

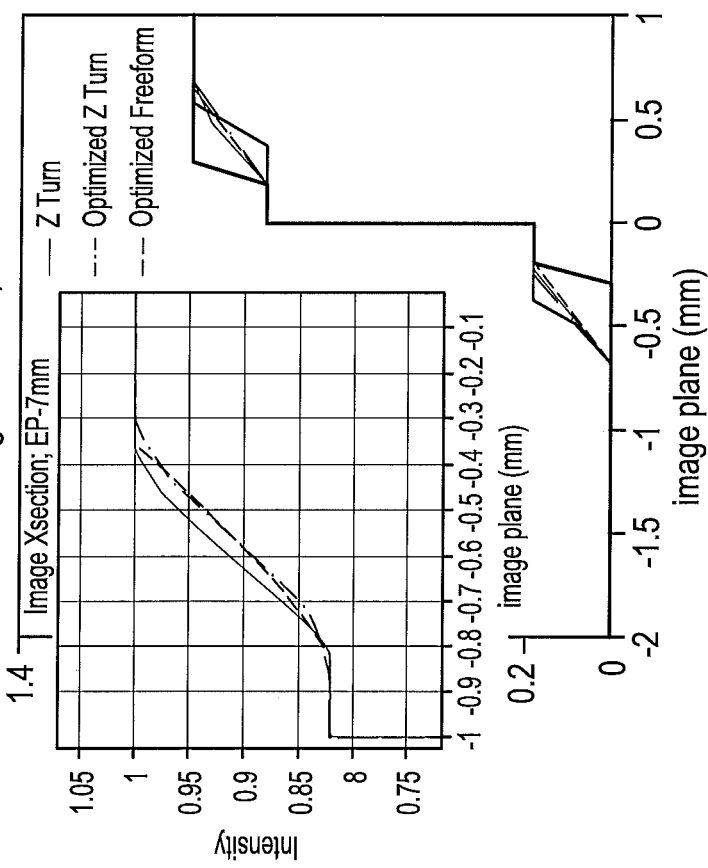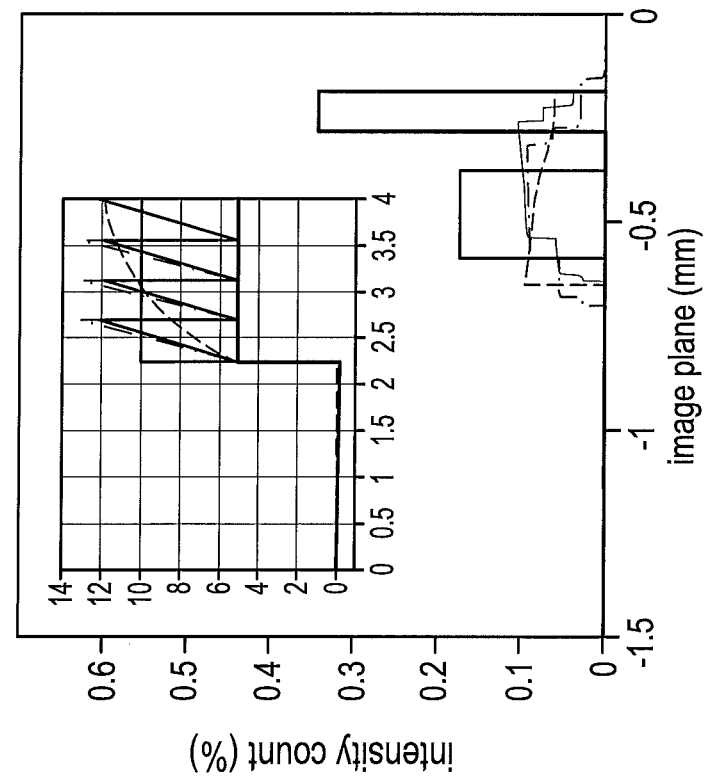
FIG. 5A
FIG. 5B

Halo

Halo

Halo

HIGH PLUS TREATMENT ZONE LENS DESIGN AND METHOD FOR PREVENTING AND/OR SLOWING MYOPIA PROGRESSION

CROSS REFERENCE TO RELATED APPLICATION

The present application is a continuation application of U.S. patent application Ser. No. 15/461,869 filed on Mar. 17, 2017, now U.S. Pat. No. 10,359,646, which is a divisional application of U.S. patent application Ser. No. 14/464,182 filed on Aug. 14, 2014, now U.S. Pat. No. 9,638,936.

BACKGROUND OF THE INVENTION

Field of the Invention

The present invention relates to ophthalmic lenses, and more particularly, to contact lenses designed to slow, retard, or prevent myopia progression. The ophthalmic lenses of the present invention comprise a high plus or high add treatment zone, thereby preventing and/or slowing myopia progression.

Discussion of the Related Art

Common conditions which lead to reduced visual acuity are myopia and hyperopia, for which corrective lenses in the form of spectacles, or rigid or soft contact lenses, are prescribed. The conditions are generally described as the imbalance between the length of the eye and the focus of the optical elements of the eye. Myopic eyes focus in front of the retinal plane and hyperopic eyes focus behind the retinal plane. Myopia typically develops because the axial length of the eye grows to be longer than the focal length of the optical components of the eye, that is, the eye grows too long. Hyperopia typically develops because the axial length of the eye is too short compared with the focal length of the optical components of the eye, that is, the eye does not grow enough.

Myopia has a high prevalence rate in many regions of the world. Of greatest concern with this condition is its possible progression to high myopia, for example greater than five (5) or six (6) diopters, which dramatically affects one's ability to function without optical aids. High myopia is also associated with an increased risk of retinal disease, cataracts, and glaucoma.

Corrective lenses are used to alter the gross focus of the eye to render a clearer image at the retinal plane, by shifting the focus from in front of the plane to correct myopia, or from behind the plane to correct hyperopia, respectively. However, the corrective approach to the conditions does not address the cause of the condition, but is merely prosthetic or symptomatic.

Most eyes do not have simple myopia or hyperopia, but have myopic astigmatism or hyperopic astigmatism. Astigmatic errors of focus cause the image of a point source of light to form as two mutually perpendicular lines at different focal distances. In the foregoing discussion, the terms myopia and hyperopia are used to include simple myopia or myopic astigmatism and hyperopia and hyperopic astigmatism respectively.

Emmetropia describes the state of clear vision where an object at infinity is in relatively sharp focus with the crystalline lens relaxed. In normal or emmetropic adult eyes, light from both distant and close objects and passing though the central or paraxial region of the aperture or pupil is focused by the crystalline lens inside the eye close to the retinal plane where the inverted image is sensed. It is observed, however, that most normal eyes exhibit positive longitudinal spherical aberration, generally in the region of about +0.50 Diopters (D) for a 5.0 mm aperture, meaning that rays passing through the aperture or pupil at its periphery are focused +0.50 D in front of the retinal plane when the eye is focused to infinity. As used herein the measure D is the dioptric power, defined as the reciprocal of the focal distance of a lens or optical system, in meters.

The spherical aberration of the normal eye is not constant. For example, accommodation (the change in optical power of the eye derived primarily though change to the internal crystalline lens) causes the spherical aberration to change from positive to negative.

As noted, myopia typically occurs due to excessive axial growth or elongation of the eye. It is now generally accepted, primarily from animal research, that axial eye growth can be influenced by the quality and focus of the retinal image. Experiments performed on a range of different animal species, utilizing a number of different experimental paradigms, have illustrated that altering retinal image quality can lead to consistent and predictable changes in eye growth.

Furthermore, defocusing the retinal image in both chick and primate animal models, through positive lenses (myopic defocus) or negative lenses (hyperopic defocus), is known to lead to predictable (in terms of both direction and magnitude) changes in eye growth, consistent with the eyes growing to compensate for the imposed defocus. The changes in eye length associated with optical blur have been shown to be modulated by changes in both scleral growth and choroidal thickness. Blur with positive lenses, which leads to myopic blur and decreases scleral growth rate, results in hyperopic refractive errors. Blur with negative lenses, which leads to hyperopic blur and increases scleral growth rate, results in myopic refractive errors. These eye growth changes in response to retinal image defocus have been demonstrated to be largely mediated through local retinal mechanisms, as eye length changes still occur when the optic nerve is damaged, and imposing defocus on local retinal regions has been shown to result in altered eye growth localized to that specific retinal region.

In humans there is both indirect and direct evidence that supports the notion that retinal image quality can influence eye growth. A variety of different ocular conditions, all of which lead to a disruption in form vision, such as ptosis, congenital cataract, corneal opacity, vitreous hemorrhage and other ocular diseases, have been found to be associated with abnormal eye growth in young humans, which suggests that relatively large alterations in retinal image quality do influence eye growth in human subjects. The influence of more subtle retinal image changes on eye growth in humans has also been hypothesized based on optical errors in the human focusing system during near work that may provide a stimulus for eye growth and myopia development in humans.

One of the risk factors for myopia development is near work. Due to accommodative lag or negative spherical aberration associated with accommodation during such near work, the eye may experience hyperopic blur, which in turn stimulates myopia progression as discussed above. Moreover, the accommodation system is an active adaptive optical system; it constantly reacts to near-objects, as well as optical designs. No matter what optical designs one puts on the eye, when the eye accommodates to near-objects, continuous hyperopic defocus will be present and make the eye myopic. Therefore, one way to design optics to slow the rate of myopia progression is to utilize a high plus signal to the retina through use of high add or plus powers.

U.S. Pat. No. 6,045,578 discloses that the addition of positive spherical aberration on the contact lens will reduce or control the progression of myopia. The method includes changing the spherical aberration of an ocular system by a direction and degree related to alter the growth in eye length, in other words emmetropization may be regulated by spherical aberration. In this process, the cornea of a myopic eye is fitted with a lens having increasing dioptric power away from the lens center. Paraxial light rays entering the central portion of the lens are focused on the retina of the eye, producing a clear image of an object. Marginal light rays entering the peripheral portion of the cornea are focused in a plane between the cornea and the retina, and produce positive spherical aberration of the image on the latter. This positive spherical aberration produces a physiological effect on the eye which tends to inhibit growth of the eye, thus mitigating the tendency for the myopic eye to grow longer.

Although the level of positive spherical aberration and/or plus power required to achieve an optimum slowdown in the myopia progression rate is unclear, researchers in the field have attempted to use multi-zone devices with regions of positive power of about +1.50 to a maximum of +3.00 D add in an attempt to slow the progression of myopia. The approach resulted in treatment results of less than about 50 percent. Treatment efficacy is defined as the relative change of axial length and/or spherical equivalent refraction from baseline for a test group compared to the change of axial length and/or spherical equivalent refraction of a control group over a year or a predetermined time period. There remains a need for a myopia control treatment with efficacy greater than 50 percent and closer to 100 percent. Intuitively adding treatment zones of high plus power would provide greater treatment as the ocular growth response in animals was proportional to the power of the optical stimulus as reported by Wildsoet, Vision Research 1995.

However, conventional wisdom in the field of bifocal or multifocal ophthalmic lenses assumes lenses with high plus or high add power may have deleterious effects on vision and contrast sensitivity as reported by Ardaya et al, Optometry 2004. Further, Smith et al (U.S. Pat. No. 7,025,460) teaches against going to powers outside the range normally found in bifocal or multifocal lenses for presbyopia. They state "It is important to note that, while the appropriate type of refractive defocus can drive eye growth (or non-growth) leading to myopia (or its regression) in the phenomenon of lens compensation, when the amount of refractive defocus is great, there may be such a large degradation in image quality due to the severe defocus that the optical state may change into the phenomenon of form deprivation and may induce myopia in that way." Further, they teach "that the maximum amount of relative curvature of field before substantial vision degradation occurs, which leads to form deprivation myopia, to be around the spherical equivalent of +3.50 D to +4.00 D, which represents the upper limit for negative curvature of field for effective treatment of myopia." This belief has discouraged researchers from pursuing high plus treatment zones for myopia control.

To the contrary, applicant's research shows that using a design with a central distance zone and a high plus or high add treatment zone having a plus power greater than about 3.00 D reduces visual acuity loss relative to low conventional plus type designs with no significant additional impact on contrast sensitivity. This is also supported in recent work by De Gracia et el, OVS 2013, although they only investigated up to 4.00 D of add power and did not relate the work to a potential benefit in myopia progression control. This breakthrough enables ophthalmic designs to achieve a meaningful greater than 50 percent slowdown in myopia progression without further negatively impacting visual acuity.

Further, significantly higher plus power relative to the distance power is not expected to lead to reduced accommodation as may occur with a lower add power design where a subject might rely to some extent on the add power for clear vision during near work activities, as has been observed during the course of our research. This reduced accommodation may lead to hyperopic defocus of rays passing through the distance portion of the device. In the current invention, the subject must accommodate over the distance portion of the lens for near vision correction as objects imaged through the treatment zones of high plus powers are sufficiently out of focus that they cannot be cleared with the accommodation-convergence system.

Another researchers in the field, R. Griffin WO2012/173891, claims to relieve accommodative lag and accommodative stresses that lead to myopia progression through the creation of an artificial pinhole that results in increased depth of focus and depth of field. In their intellectual property, "the eye's accommodation is more relaxed" in contrast to the present invention.

With reference now to FIG. 1, the graph illustrates a device with a design that incorporates a distance zone to correct for distance vision and a peripheral zone of variable plus power. Visual acuity was measured using a four forced choice method with progressively smaller Snellen optotypes. Increasing peripheral plus power to about +2.00 D to +3.00 D causes an increasing loss of high contrast visual acuity, as typical of multifocal type designs for presbyopes. As the peripheral power continues to increase; however, the relative effect on visual acuity surprisingly improves and plateaus, so that by above about +4.00 D to +5.00 D peripheral plus, the visual acuity loss becomes relatively constant. This is of significance for the design of myopia control lenses, since higher plus power is found (with animal models) to have a greater impact on eye growth, as reported in Wildsoet, Vision Research 1995.

However, further optimization of plus power designs is required to optimize image quality. With reference now to FIG. 2, power profiles are illustrated having +5.00 D or +10.00 D power beyond a 2.25 mm radial location from a center of a lens. Rays passing through these high plus or high add power regions form sharp foci in front of the retina. However, due to continued propagation to the retina, these rays form a ring-like defocus blur on the retina.

As shown in the point spread function (PSF) cross section of FIG. 3, rays coming from the +5.00 D and +10.00 D regions form separate spikes on the retina. Thus, if one looks at a point light source through one of these +5.00 D or +10.00 D high plus lenses, his/her retina would receive a peak signal surrounded by a ring-like halo. Usually, this is not a problem when one reads letters or resolves fine details of objects because the halo is so dim that the human doesn't perceive it. Nevertheless, this is a problem if a person looks at a black/white edge, as energy from the white background can leak into the black due to the presence of the spike in PSF.

With reference now to FIG. 4, the image cross section for the +5.00 D and +10.00 D power profiles of FIG. 2 at an entrance pupil size of 6.0 mm are shown by convolving the PSF with the black/white edge in object space. A lens having 0.00 D power forms a sharp edge between the black and white (at 0.0 mm location) and thus doesn't have a ring-like structure. On the other hand, the lenses with +5.00 D and +10.00 D regions do not have a sharp edge between black and white, thereby resulting in images in which the black background is not completely black, and the white background is not completely white.

Accordingly, the presence of halo is an inherent property of high plus or high add lens designs. The present invention is directed to lenses having high plus power treatment zones that are suitable for the use in treating, controlling, or reducing the progression of myopia while also minimizing a halo effect.

SUMMARY OF THE INVENTION

The lens design of the present invention overcomes the limitations of the prior art by providing lenses that ensure distance vision correction and have high plus power treatment zones that treat, control, or reduce the progression of myopia while also minimizing a halo effect.

In accordance with one aspect, the present invention is directed to an ophthalmic lens for at least one of slowing, retarding or preventing myopia progression and for minimizing a halo effect. An ophthalmic lens comprises a center zone with a negative power for myopic vision correction and at least one treatment zone surrounding the center zone. The at least one treatment zone has a power profile that increases from an outer margin of the center zone to a positive power within the at least one treatment zone of greater than +5.00 D. For optimum distance correction, the power profile within the distance power region can be flat based on subject correction requirement or progressively vary to account for the cornea positive or negative spherical aberration.

In accordance with another aspect, the present invention is directed to a method for at least one of slowing, retarding or preventing myopia progression. An ophthalmic lens is provided comprising a center zone with a negative power for myopic vision correction and at least one treatment zone surrounding the center zone, the at least one treatment zone having a power profile that increases from an outer margin of the center zone to a positive power within the at least one treatment zone of greater than +5.00 D. Accordingly, the growth of the eye is altered. For optimum distance correction, the power within the distance power region can be flat based on subject correction requirement or progressively vary to account for the cornea positive or negative spherical aberration.

The contact lens of the present invention is designed with a power profile having at least one high plus or high add treatment zone. As set forth herein, the at least one treatment zone minimizes a halo effect at a black/white edge.

The lens design of the present invention may also be customized to achieve both good foveal vision correction and higher treatment efficacy based on the subject's average pupil size.

The high plus contact lens design of the present invention provides a simple, cost-effective and efficacious means and method for preventing and/or slowing myopia progression which is increasing throughout the world.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 5a illustrates a point spread function for five power profiles.

FIG. 5b illustrates the image cross section of the power profiles of FIG. 5a.

DETAILED DESCRIPTION OF THE INVENTION

In accordance with the present invention, an ophthalmic lens has at least one high plus or high add treatment zone surrounding a center zone for treating, preventing, or slowing myopia progression while also minimizing any halo effect at a black/white edge.

With reference now to FIG. 5a (inset graph), five power profiles are illustrated: 1) a power profile having a +5.00 D treatment zone; 2) a power profile having a +10.00 D treatment zone; 3) two zig-zag or sawtooth power profiles with periodic power modulation between about +5.00 D and about +12 D; and 4) a power profile having a gradual power increase from +5.00 D to +12.00 D.

In the PSF cross section of FIG. 5a (main graph), the two ring spikes of the +5.00 D and +10.00 D add power profiles have a much higher intensity than the other three power profiles, because the latter three designs have continuous power modulation. On the other hand, the latter three designs carry wider ring spikes. The convolution between the spikes with wider width and lower intensity yields a smooth transition of halo intensity between black and white edges, as shown in FIG. 5b (inset graph), as compared to the sharp edges for the +5.00 D and +10.00 D power profiles, as shown in the main graph of FIG. 5b. As a result of the smooth transition, human vision finds any halo effect for the latter three power profiles less bothersome than the halo effect resulting from the abrupt intensity profiles.

Figure 1:
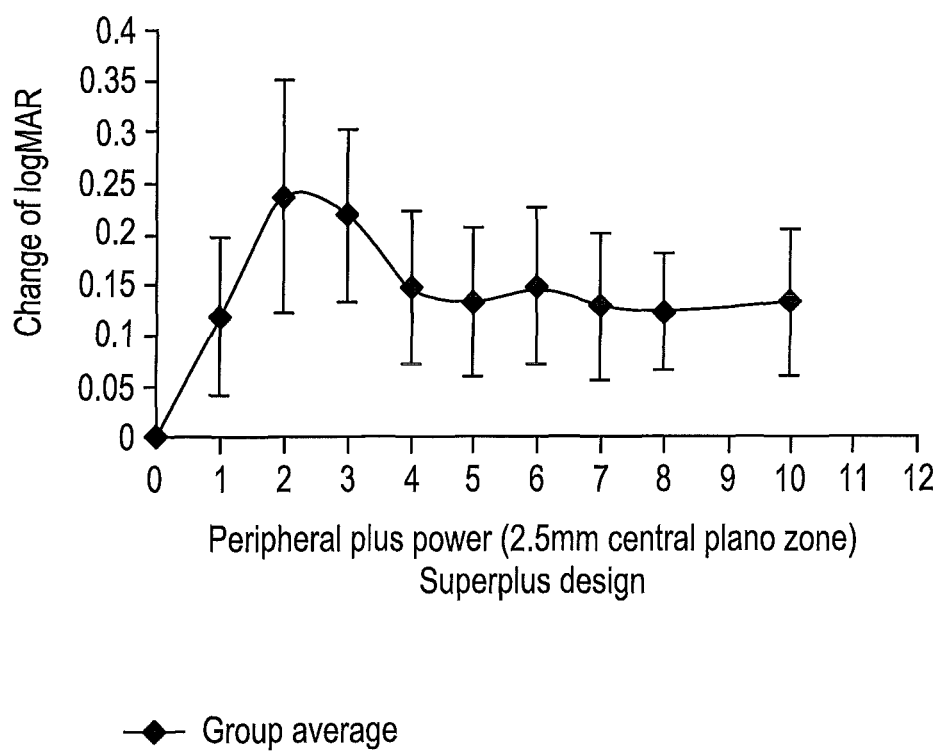
FIG. 1 illustrates a graph showing changes in visual acuity as plus power is added in a peripheral zone.
Figure 2:
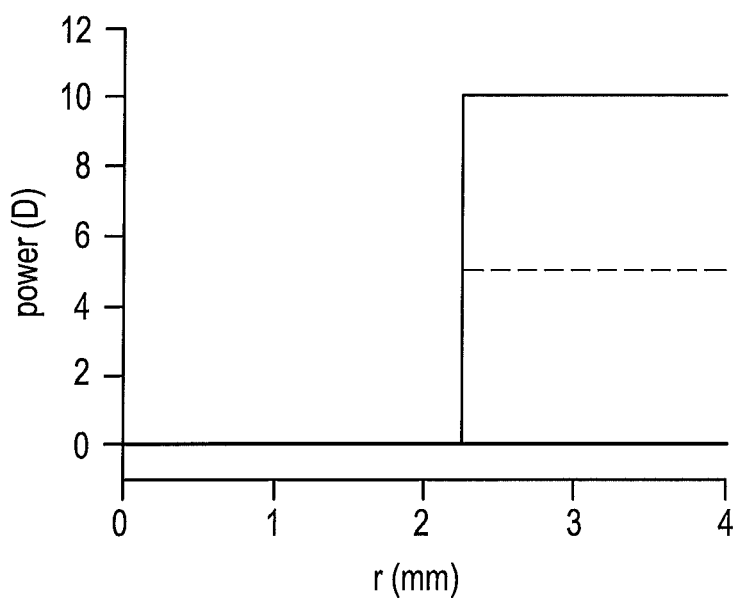
FIG. 2 illustrates power profiles of two lenses, one having a +5.00 D treatment zone and the other having a +10.00 D treatment zone.
Figure 3:
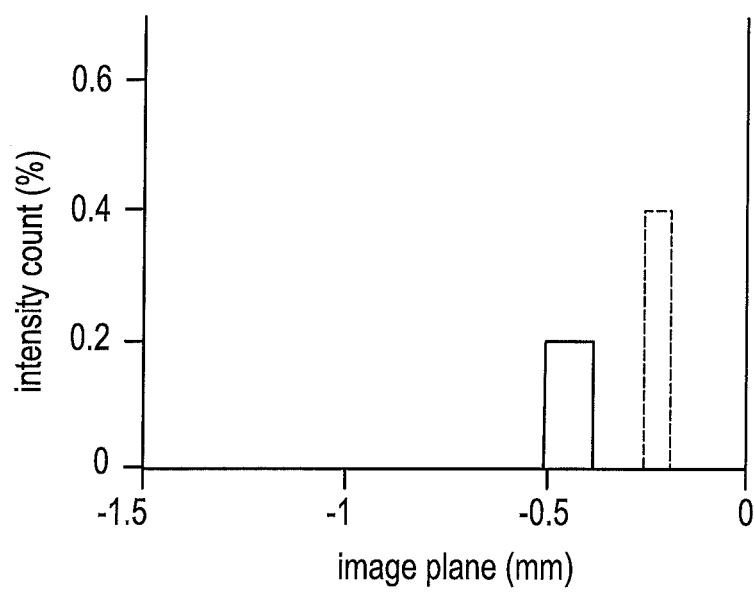
FIG. 3 illustrates a cross section of the point spread function for the power profiles of FIG. 2 at an entrance pupil size of 6.0 mm.
Figure 4:
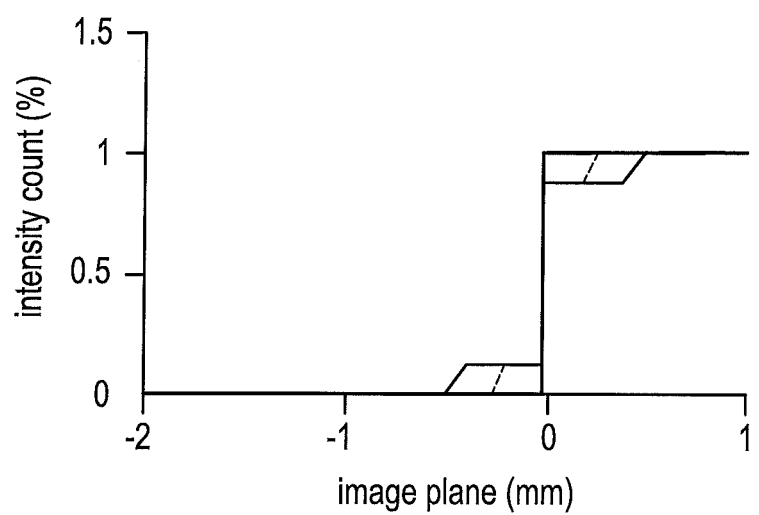
FIG. 4 illustrates an image cross section of the power profiles of FIG. 2.
Figure 6A:
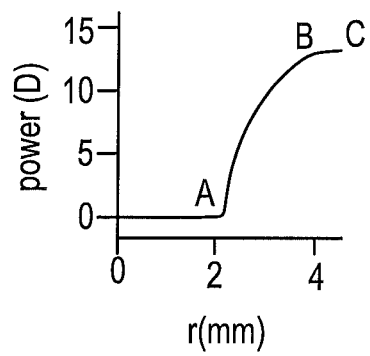
FIGS. 6a-c illustrates power profiles of three lenses according to the present invention.
Figure 6B:
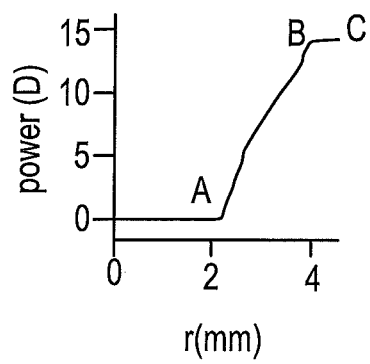
Figure 6C:
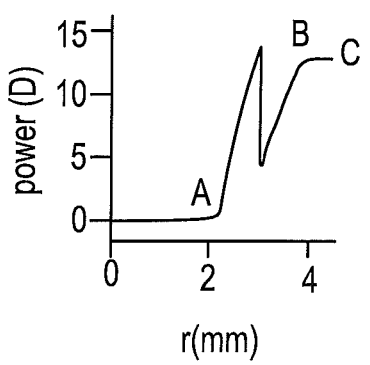

With reference now to FIGS. 6a-6c, the power profiles of three lens designs according to the present invention are illustrated. For each design, the power profile comprises a center zone, which may have a negative focal power to correct existing a myopic distance vision condition (i.e., paraxial power). The diameter of the center zone may be about 3 mm to about 7 mm, for example 4.3 mm. Each lens design also comprises at least one treatment zone that surrounds the center zone. The at least one treatment zone carries a large amount of high add or high plus power relative to the power in the center zone.

As illustrated in FIGS. 6a-b, the power profiles rise gradually and continuously from a margin of the center zone (point A) to a point within the at least one treatment zone (point B). In specific embodiments, the location of point B is between 3.0 mm and 4.5 mm from a center of the lens. The at least one treatment zone may remain constant from point B to a margin of an optic zone (point C, for example at 4.5 mm). As illustrated in FIG. 6c, the power profile may zig-zag or oscillate as the power rises from point A to point B and/or point C and does not need to be monotonic. In specific embodiments, the at least one treatment zone may have a dioptric power ranging from about +1 D to about +15 D.

Figure 7A:
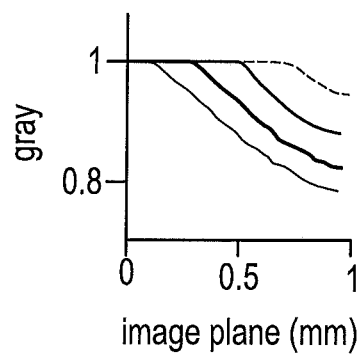
FIGS. 7a-c illustrates the image cross section of the power profiles of FIGS. 6a-c, respectively.
Figure 7B:
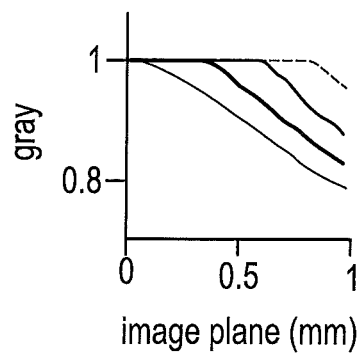
Figure 7C:
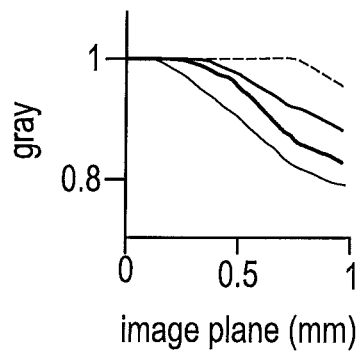

According to the present invention, a gradual and/or periodic change of plus power in the at least one treatment zone mitigates the halo effect because such variations smoothen the intensity profile at sharp black and white edges. The halo intensity profiles of the three lens designs of FIGS. 6a-c are shown in FIGS. 7a-c, respectively. All three designs have a smooth halo intensity profile at the black/white edge.

While lenses of the present invention are designed so that the halo becomes less bothersome to the human eye, it may be difficult to reduce the halo effect when the lens becomes decentered on the eye. When a lens decenters, the ring-like structure in PSF becomes asymmetric, and energy will shift from one side of PSF to another side. As a result, one side of ring-like structure in PSF will have a much higher intensity, and the halo intensity will increase. The halo will become obvious regardless of the halo intensity profile. Hence, the utilized lens geometrical design should preferably result in good lens centration on the eye to further minimize potential for the visual artifacts.

Figure 8A:
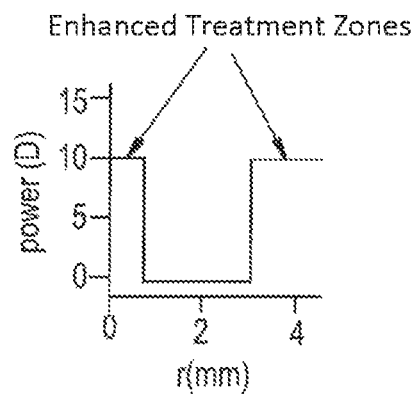
FIGS. 8a-c illustrates power profiles of three additional lenses according to the present invention.
Figure 8B:
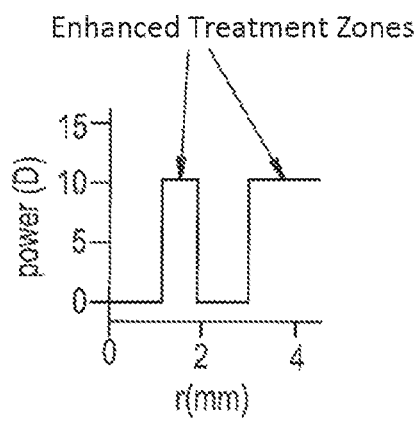
Figure 8C:
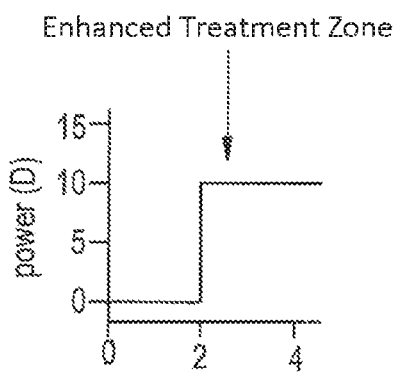

With reference now to FIGS. 8a-c, the power profiles for three additional lens designs according to the present invention are illustrated. These three lens designs have 1) at least one enhanced treatment zone in which power is added within the center zone, and 2) at least one treatment zone. The at least one enhanced treatment zone may vary in width from about 0.5 mm to about 1.0 mm and may be positioned at the center of the lens (FIG. 8a) or be positioned as a peripheral ring around the center within a 2 mm radius of the center of the lens (FIG. 8b). The at least one treatment zone may have a gradual and/or period change in plus or ADD power as discussed above or may have a stepped increase in plus or ADD power. The power magnitude of the at least one treatment zone may range from about +5 D to about +15 D.

Figure 9:
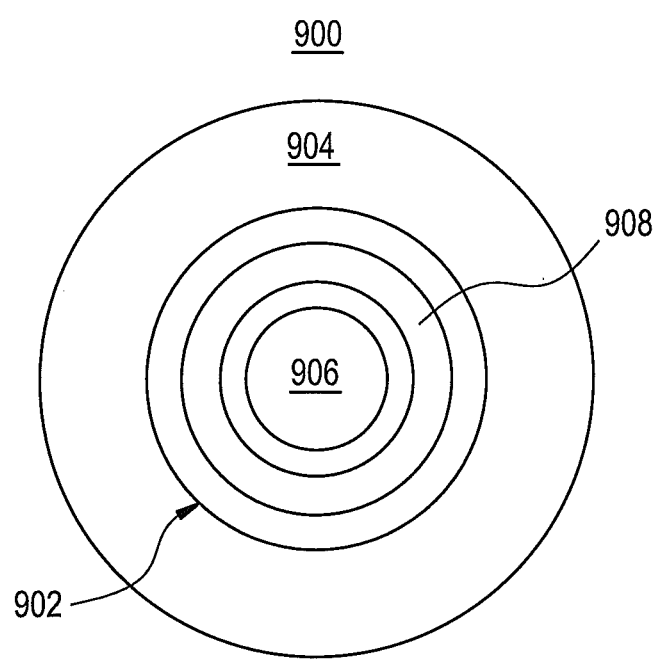
FIG. 9 is a diagrammatic representation of an exemplary contact lens in accordance with the present invention.

Referring now to FIG. 9, there is illustrated a schematic diagrammatic view of a contact lens 900 in accordance with an embodiment of the present invention. The contact lens 900 comprises an optic zone 902 and an outer zone 904. The optic zone 902 comprises a first, center zone 906 and at least one peripheral zone 908. In specific embodiments, the diameter of the optic zone 902 may be selected to be 8.0 mm, the diameter of the substantially circular first zone 906 may be selected to be 4.0 mm, and the boundary diameters of an annular outer peripheral zone 908 may be 5 mm and 6.5 mm as measured from the geometric center of the lens 900. It is important to note that FIG. 9 only illustrates an exemplary embodiment of the present invention. For example, in this exemplary embodiment, the outer boundary of the at least one peripheral zone 908 does not necessarily coincide with the outer margin of the optic zone 902, whereas in other exemplary embodiments, they may coincide. The outer zone 904 surrounds the optic zone 902 and provides standard contact lens features, including lens positioning and centration. In accordance with one exemplary embodiment, the outer zone 904 may include one or more stabilization mechanisms to reduce lens rotation when on eye.

It is important to note that the various zones in FIG. 9 are illustrated as concentric circles, the zones may comprise any suitable round or non-round shapes such as an elliptical shape.

It is important to note that as the entrance pupil size of the eye varies among subpopulations, in certain exemplary embodiments, the lens design may be customized to achieve both good foveal vision correction and myopic treatment efficacy based on the patient's average pupil size. Moreover, as pupil size correlates with refraction and age for pediatric patients, in certain exemplary embodiments, the lens may be further optimized towards subgroups of the pediatric subpopulation with specific age and/or refraction based upon their pupil sizes. Essentially, the power profiles may be adjusted or tailored to pupil size to achieve an optimal balance between foveal vision correction and minimization of halo effect resulting from a high plus or high add treatment zone.

Currently available contact lenses remain a cost effective means for vision correction. The thin plastic lenses fit over the cornea of the eye to correct vision defects, including myopia or nearsightedness, hyperopia or farsightedness, astigmatism, i.e. asphericity in the cornea, and presbyopia, i.e., the loss of the ability of the crystalline lens to accommodate. Contact lenses are available in a variety of forms and are made of a variety of materials to provide different functionality.

Daily wear soft contact lenses are typically made from soft polymer materials combined with water for oxygen permeability. Daily wear soft contact lenses may be daily disposable or extended wear disposable. Daily disposable contact lenses are usually worn for a single day and then thrown away, while extended wear or frequent replacement disposable contact lenses are usually worn for a period of up to thirty days. Colored soft contact lenses use different materials to provide different functionality. For example, a visibility tint contact lens uses a light tint to aid the wearer in locating a dropped contact lens, enhancement tint contact lenses have a translucent tint that is meant to enhance one's natural eye color, the color tint contact lens comprises a darker, opaque tint meant to change one's eye color, and the light filtering tint contact lens functions to enhance certain colors while muting others. Rigid gas permeable hard contact lenses are made from siloxane-containing polymers but are more rigid than soft contact lenses and thus hold their shape and are more durable. Bifocal contact lenses are designed specifically for patients with presbyopia and are available in both soft and rigid varieties. Toric contact lenses are designed specifically for patients with astigmatism and are also available in both soft and rigid varieties. Combination lenses combining different aspects of the above are also available, for example, hybrid contact lenses.

It is important to note that the lens designs of the present invention may be incorporated into any number of different contact lenses formed from any number of materials. Specifically, the lens design of the present invention may be utilized in any of the contact lenses described herein, including, daily wear soft contact lenses, rigid gas permeable contact lenses, bifocal contact lenses, toric contact lenses and hybrid contact lenses. In addition, although the invention is described with respect to contact lenses, it is important to note that the concept of the present invention may be utilized in spectacle lenses, intraocular lenses, corneal inlays and onlays.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic lens for at least one of slowing, retarding or preventing myopia progression in a patient, the ophthalmic lens comprising:
   a treatment zone with a negative dioptric power adapted to correct myopic vision of said patient; and
   at least one enhanced treatment zone having an ADD power relative to said negative dioptric power of said treatment zone, wherein said ADD power is between +5 D and +15 D,
   wherein the at least one enhanced treatment zone is positioned at a center of said ophthalmic lens and extends to a radius of about 0.7 mm from said center.

2. The ophthalmic lens according to claim 1, wherein the ADD power within said enhanced treatment zone is between +10 D and +15 D.

3. The ophthalmic lens according to claim 1, wherein the ADD power within said enhanced treatment zone is a stepped increase in add power.

4. The ophthalmic lens according to claim 1, further comprising a second enhanced treatment zone having an ADD power relative to said negative dioptric power of said treatment zone.

5. The ophthalmic lens according to claim 1, wherein said enhanced treatment zone has a radius of 0.75 mm.

* * * * *